United States Patent [19]

Findlay

[11] 4,065,504

[45] Dec. 27, 1977

[54] PROCESS FOR THE METHYLATION OF HYDROXYBENZENE DERIVATIVES

[75] Inventor: David Michael Findlay, Terrasse Vaudreuil, Canada

[73] Assignee: Domtar Limited, W. Montreal, Canada

[21] Appl. No.: 692,788

[22] Filed: June 4, 1976

[51] Int. Cl.$^2$ .................... C07C 41/00; C07C 45/00
[52] U.S. Cl. ................... 260/600 R; 260/592; 260/521 B
[58] Field of Search ............ 260/600, 592, 612 D, 260/613 D

[56] References Cited

U.S. PATENT DOCUMENTS 3,855,306  12/1974  Wehrli .................. 260/600
3,867,458  2/1975  Imai et al. .............. 260/600

OTHER PUBLICATIONS

Blatt, Organic Synthesis, Collective vol. II, (1943), pp. 619–621.

Primary Examiner—Bernard Helfin
Attorney, Agent, or Firm—C. A. Rowley

[57] ABSTRACT

A method is disclosed of alkylating substituted hydroxybenzenes, particularly substituted hydroxybenzaldehydes, by reacting the hydroxybenzene compound with a dialkylsulfate in the presence of an alkali metal carbonate, substantially in the absence of a solvent. The alkoxylated product is obtained in yields substantially close to theoretical.

10 Claims, No Drawings

PROCESS FOR THE METHYLATION OF HYDROXYBENZENE DERIVATIVES

FIELD OF THE INVENTION

The present invention relates to the alkylation of substituted hydroxybenzenes to form alkoxylated derivatives. It is concerned particularly with an improved method of preparation of methoxylated or ethoxylated substituted hydroxybenzenes.

PRIOR ART

It is known to methylate phenol to anisole using dimethyl sulfate in an alkaline aqueous medium. (Ind. & Eng. Chemistry, Vol. 22, p. 34, January 1930). A method of making veratraldehyde from vanillin is described by J. S. Buck in "Organic Syntheses" (Vol. II, Wiley, 1943, p. 619) and the same method was used for the methylation of 5-hydroxyvanillin to 3,4,5,-trimethoxybenzaldehyde (Journal of American Chemical Society 74, 1952 p. 4263) and for the methylation of syringealdehyde to 3,4,5,-trimethoxybenzaldehyde (Journal of American Chemical Society 76, 1954, p. 5555). These procedures generally involve making aqueous solutions of the respective hydroxybenzaldehyde in the presence of alkali, and the use of substantial excesses of dimethyl sulfate as the methylating agent. Since the benzaldehydes are sparingly soluble in water, substantial quantities of water had to be used in these procedures. Yields of 82 – 87% were generally obtained.

U.S. Pat. No. 3,855,306 discloses methylation of 5-hydroxyvanillin (initially prepared from vanillin by bromination and subsequent hydrolysis) with dimethyl sulfate in the presence of an alkali carbonate in an organic medium such as acetone. 3,4,5,-Trimethoxybenzaldehyde in yields of about 94% are obtained in this method, but the reaction is slow and operating with organic solvents presents disadvantages of operation and cost.

BRIEF DESCRIPTION OF THE INVENTION

I have found that when a substituted hydroxybenzene as herein defined is reacted with a dialkyl sulfate in the presence of an alkali metal carbonate, at a temperature at which said substituted hydroxybenzene and the dialky sulfate form a liquid medium in which said carbonate is suspended, substantially in the absence of a solvent, a substituted alkoxybenzene is obtained in high yield in a relatively short reaction time. In particular, when a hydroxybenzaldehyde as herein defined is mixed with dimethyl sulfate and an alkali metal carbonate, substantially in the absence of a solvent, and the mixture is heated to a temperature at which said substituted hydroxybenzaldehyde and the dimethyl sulfate form a substantially homogeneous liquid medium and said carbonate is suspended in said medium whereby a substantially fluid slurry is obtained, and the said slurry is maintained at or above said temperature with agitation, methoxybenzaldehyde is obtained in substantially quantitative yields. Still more particularly, excellent yields of 3,4,5,-trimethoxybenzaldehyde are obtained by reacting a substituted hydroxybenzaldehyde, such as syringealdehyde or hydroxyvanillin, with dimethyl sulfate in the presence of sodium carbonate and substantially in the absence of a solvent in accordance with the invention.

Accordingly, in its broadest aspect the invention provides a process wherein a substituted hydroxybenzene is mixed with a dialkyl sulfate and an alkali metal carbonate, to form a reaction mixture, the mixture is fluidized, preferably by heating to a temperature at which said substituted hydroxybenzene and said dialkyl sulphate form a liquid medium and said carbonate is suspended in said medium, the heating is continued with agitation until the alkylation reaction is completed. A substituted alkoxybenzene is obtained in substantially quantitative yield and can be separated from the reaction mixture.

DETAILED DESCRIPTION OF THE INVENTION

The term substituted hydroxybenzene, as used herein, will denote single ring aromatic compounds having at least two substituents on the ring, one of which substituents will necessarily be a hydroxyl and any of the other substituents will be a member of the group consisting of formyl, keto, hydroxyl, carboxyl, lower alkyl, lower alkoxyl and halogen substituents. Examples of such compounds are hydroxybenzaldehyde, vanillin, vanillin acid, aceto-vanillone, syringealdehyde, syringic acid, acetosyringeone, gallic acid, and the like. A preferred group of compounds consists of substituted hydroxybenzaldehydes having on the ring in addition to the hydroxyl and formyl substituents, one or two additional substituents, preferably additional hydroxy or methoxy substituents. Examples of the latter group of compounds include in particular vanillin (3-methoxy-4-hydroxybenzaldehyde), 5-hydroxyvanillin, 3,4-dihydroxybenzaldehyde, syringealdehyde (3,5-dimethoxy-4-hydroxybenzaldehyde), and mixtures of the above. The invention is of particular interest in the preparation of 3,4,5-trimethoxybenzaldehyde from syringealdehyde or from 5-hydroxyveratraldehyde, or from 5-hydroxyvanillin and the method will be particularly described with reference to syringealdehyde as starting material. However, it will be evident from the description that other substituted hydroxybenzenes and particularly substituted hydroxybenzaldehydes of the type described can be used. These substituted hydroxybenzenes and particularly substituted hydroxybenzaldehydes, are generally solid at room temperature, and as they are generally of low solubility in water or alkali, very substantial quantities of water have to be used to carry out the alkylation in solution, in accordance with the prior art. It has been found that the use of large quantities of water is deleterious to the yield of the alkoxylated product and an important feature of the present invention is precisely that the reaction is carried out without dissolving the initial substituted hydroxybenzene starting material, either in water or in an organic solvent. A relatively small amount of water may have to be added in the course of the reaction when the methoxylated product begins to form in quantity, as will be explained below, but the quantities involved are so small that they no longer affect deleteriously the yield.

Preferred alkylation reagents for use in the invention are dimethyl sulfate and diethyl sulfate. As the reaction proceeds one of the methyl or ethyl groups of the dimethyl or diethyl sulfate respectively is used up, and in the presence of alkali is replaced on the sulfate by the alkali metal present. As alkaline agent it is preferred to use an alkali metal carbonate, such as sodium or potassium or lithium carbonate. Generally a moderate excess of dialkyl sulfate over the theoretical amount needed for complete alkylation of the hydroxyl group or groups present on the hydroxybenzaldehyde, will be used. Thus the molar proportion of dimethyl or diethyl sulfate to the substituted hydroxybenzene compound will such that there will be between 1.1 and 2 mols of the alkylating agent for each mol equivalent of the hydroxybenzene compound. The amount of carbonate will be controlled to keep the reaction mixture neutral or alkaline at all times and a molar ratio of 1 - 2 of carbonate to 1 mol equivalent of the hydroxybenzene compound will be required.

In carrying out the invention the substituted hydroxybenzene compound is mixed with the normally liquid dimethyl or diethyl sulfate and with the carbonate, the mixture at room temperature having the consistency of a thick heavy paste, which does not lend itself to stirring or mixing. However, when the mixture is heated to a temperature above room temperature but generally still well below the melting point of the hydroxybenzene compound, said compound forms with the normally liquid dimethyl or diethyl sulfate a homogeneous liquid medium in which the carbonate is suspended and the thus formed slurry is of a creamy, fluid, easily stirrable consistency. Whether the formation of the homogeneous mixture is due to enhanced solubility of the hydroxybenzene compound in the dialkyl sulfate present or to fusion of said compound at temperatures above room temperature, or to both causes, has not been established with certainty. In any case the temperature at which the formation of a homogeneous fluid mixture of the hydroxybenzene compound with the alkylating agent occurs, as above stated, is generally below the normal melting point of the hydroxybenzene compound. In certain cases, as in Example 5 hereinbelow, a homogeneous liquid mixture of the hydroxybenzene compound with the diethyl sulfate forms almost at room temperature, but in most cases somewhat higher temperatures are required. For instance, when syringealdehyde is mixed with dimethyl sulfate in the presence of sodium carbonate, the mixture is initially a thick paste which becomes fluid when the temperature is raised to about 75° C and from this point the mixture is fluid enough to be thoroughly mixed. The reaction will generally be carried out at a temperature at least equal to said fluidizing temperature and preferably at a temperature between 60° C and 120° C. In the above mentioned case of syringealdehyde with dimethyl sulfate and sodium carbonate it is preferred to carry out the reactions at a temperature between 75° and 100°, while the mixture is thoroughly agitated.

As the alkylation proceeds the dimethyl or diethyl sulfate is consumed and the mixture thickens to the point where difficulties may be experienced in maintaining the agitation. It may then be desirable, as mentioned above, to add slowly very small amounts of water in quantities just sufficient to maintain the mass stirrable. The quantities of water are extremely small in comparison with the quantities of water needed when the solution method of the prior art is used in fact, the difference is an order of magnitude or more. Generally, the total quantity of water that may be used in the present invention for the purpose of maintaining the reaction mass in a state of sufficient fluidity for mixing will be at most equal to, but usually considerably less than, the initial weight of the hydroxybenzene compound. In the solution methods of the prior art the quantity of water was such as to dissolve the hydroxybenzene compound and when it is considered that the solubility in water of, for instance, vanillin, or syringealdehyde even in the presence of alkali, is relatively low, it will be appreciated that the quantities of water used in the prior art were vastly greater, (about 8-15 times more) than even the maximum quantity of water that may have to be used in the present invention. In the present invention even this small amount of water is added in small portions, and only when required, as it serves essentially only as a sort of lubricant, to fluidize somewhat and facilitate the agitation of the reaction mixture when the mixture thickens with the progress of the reaction.

The reaction takes about one to four hours to complete and very high yields, in many cases substantially at or close to 100% of the theoretical, are obtained. To determine the completion of the reaction samples may be taken from time to time from the reaction mixture and analyzed. After the reaction is completed, the alkylated products are separated essentially in a known manner. For example hot water may be added to the reaction mixture to maintain it in the liquid state and the organic material removed by separation of phases; alternatively, the organic phase can be extracted from the mixture with an organic solvent. Alternatively still, cool water may be added to the mixture, or after adding hot water the mixture may be cooled, and the organic products may be removed in the solid state by filtration or contrifuging. It may be desirable to acidify the mixture after the addition of water, e.g. with hydrochloric or sulfuric acid, to reduce the solubility in water of the unreacted organic material.

The following Examples are provided to further illustrate the invention it being understood that they will not be interpreted as limiting the invention in any way to the particulars disclosed therein.

EXAMPLE 1

A mixture of 100g of syringealdehyde (0.55 mol), 85.0g of sodium carbonate (0.80 mol) and 106.0g of dimethyl sulfate (0.84 mol) was placed in a round-bottomed flask equipped with a reflux condenser, a stirrer and a dropping funnel. The syringealdehyde was of about 99% purity and was obtained, by distillation, from a crude mixture of vanillin and syringealdehyde produced by alkaline oxidation of waste Kraft liquor. The dimethyl sulfate was of commercial quality (B.P. 75°-77°/15 mm) and the sodium carbonate was of reagent grade in some experiments and of commercial grade in others. The flask was kept in a silicone oil bath on a hot plate. The mixture as prepared at room temperature was a thick paste which could be kneaded but could not be mixed by the stirrer driven by an electric motor. When the temperature of the mixture reached 75° C the mixture became fluid and was easily stirred by the blades of the stirrer. The temperature was further raised to about 85° C and maintained at this temperature with stirring for a total of about 2 hours. After the initial 35 minutes of this period the reaction mixture began to thicken due to the consumption of dimethyl sulfate and, in order to maintain it fluid, water in 5 gram portions was added from time to time through the funnel while the stirring continued. In total about 60g of water were added to the mixture during the reaction period.

At the end of two hours, the heating was discontinued and about 500 ml of hot water was added to the mixture. The mixture was acidified with concentrated hydrochloric acid and was then extracted three times with about 250 ml of benzene and the combined extract was washed with water. The benzene was removed by distillation and the solid product was dried in a vacuum oven and weighed. The yield was 106.9 g of 3,4,5-methoxybenzaldehyde, representing a yield of 99.3% of the theoretical. Analysis by gas-liquid chromatography (g.l.c.) showed a purity of 99.85% with syringealdehyde as the only detectable impurity.

EXAMPLE 2

50g of syringealdehyde (0.275 mol) 40g of sodium carbonate (0.38 mol) and 53.4g of dimethyl sulfate (0.42 mol) were placed in a round-bottom flask and heated substantially as in Example 1. When the temperature reached 75° C the reaction mixture became fluid but after 30 minutes at a temperature between 80° and 87° it began to thicken again. 30 ml. of water was then added dropwise while the temperature was maintained for 1.2 hours. On completion of the reaction 250 ml of hot water was added to the mixture. Then the mixture was cooled, the solidified organic material separated by filtration, washed with water and vacuum dried. The yield of 3,4,5-trimethoxybenzaldehyde was 99.6% with about 0.4% syringealdehyde remaining.

EXAMPLE 3

The conditions of Example 2 were repeated with the difference that the reaction mixture was maintained at a temperature between 85° C and 95° and that it was maintained at this temperature for 3.6 hours. The yield of 3,4,5-trimethoxybenzaldehyde was substantially quantitative with not more than 0.02% syringealdehyde remaining.

EXAMPLE 4

25.0g syringealdehyde (0.137 mol), 26.6g of dimethyl sulfate (0.211 mol), and 27.7 g. of potassium carbonate (0.201 mol) were heated with stirring as in Example 1. When the temperature reached 45° C the mixture became fluid and carbon dioxide was given off. The temperature was slowly increased to 75° C and held at this value for 1 hour. Addition of water, acidification, and benzene extraction gave a quantitative yield of 3,4,5-trimethoxybenzaldehyde which contained no detectable syringealdehyde or other impurities as determined by g.l.c. analysis.

EXAMPLE 5

100 g of vanillin (0.658 mol), 128 g of dimethyl sulfate (1.00 mol), and 96.0 g of sodium carbonate (0.91 mol) were heated with stirring to 80° C over b 0.5 hr. Stirring was continued at this temperature for 1.0 hr. over which time 60 ml of water were added in 5 ml portions. Work-up as in Example 1 gave a quantitative yield of veratraldehyde which contained not more than 0.1% vanillin, as determined by g.l.c. analysis.

EXAMPLE 6

On mixing 50 g of vanillin (0.329 mol), 48.0 g of sodium carbonate (0.453 mol), and 60.2 ml of diethyl sulfate (0.460 mol) a fluid mixture was obtained almost immediately. The mixture was maintained at 80° for 3.5 hr. Water (25 ml) was added in small portions over the last 2.0 hr. Work-up as in the previous examples yielded 58.06 gm. (98.1%) of 4-ethoxy-3-methoxybenzaldehyde which contained 2.4% vanillin.

EXAMPLE 7

20 g of p-hydroxybenzaldehyde (0.164 mol) was reacted with 29.0 g of dimethyl sulfate (0.230 mol) and 22.0 g of sodium carbonate (0.20 mol) for 2 hr. at 75°-80° C. A total of 12 ml of water was added in small portions over the last hour. Work-up by addition of water, acidification and benzene extraction yielded 22.27 g of p-methoxybenzaldehyde (99.9%) containing not more than 0.1% p-hydroxybenzaldehyde.

EXAMPLE 8

20 g of gallic acid (0.294 mol) was methylated with 222 g of dimethyl sulfate (1.765 mol) in the presence of 160 g of sodium carbonate (1.51 mol) by heating to 100° C for 4 hr. The reaction mixture remained sufficiently fluid to allow stirring without any addition of lubricant water. Separation of the neutral and alkali soluble material by addition of water, extraction with benzene, and then acidification and extraction with benzene yielded 67.95 g (94.7%) of methyl 3,4,5-trimethoxybenzoate (the completely methylated product) and 2.1 g of partially methylated, alkali soluble material.

EXAMPLE 9

5 g of syringic acid (0.025 mol), 9.23 g of dimethyl sulfate (0.073 mol), and 7.0 g of sodium carbonate (0.066 mol) were heated to 95° C for 3.0 hr. Work-up as in Example 7 yielded 5.51 g (96.5%) of methyl 3,4,5-trimethoxybenzoate and 0.115 g of partially methylated material.

EXAMPLE 10

5 g of o-vanillin (.033 mol) was reacted with 4.8 gm. of sodium carbonate (0.045 mol) and 6.2 gm. of dimethyl sulfate (0.05 mol) by heating to 80°-85° C for 2.5 hr. G.l.c. analysis indicated that 95.4% of the o-vanillin had been converted to 2,3-dimethoxybenzaldehyde.

EXAMPLE 11

10 g of acetovanillone (0.06 mol) was methylated with 10.25 g of dimethyl sulfate (0.083 mol) and 8.0 g of sodium carbonate. The reaction mixture was stirred at 80°-90° C for 2 hr. while 6 ml of water were added dropwise over the last 1.2 hr. Addition of water, acidification, and extraction with benzene produced a nearly quantitative yield of 2,4-dimethoxyacetophenone containing less than 0.3% acetovanillone.

What I claim is:
1. A method of preparing a carbonyl-substituted alkoxybenzene comprising
  a. forming a mixture consisting essentially of a carbonyl-substituted hydroxybenzene, a dialkyl sulfate and sodium carbonate, said carbonyl-substituted hydroxybenzene being one of the class consisting of hydroxybenzaldehyde, di-hydroxybenzaldehyde, vanillin, hydroxyvanillin, syringealdehyde, hydroxyveratraldehyde, acetovanillone and acetosyringeone, and said dialkyl sulphate being one of the group consisting of dimethyl sulfate and diethyl sulfate, the molar ratios of said dialkyl sulfate and of said sodium carbonate to said hydroxybenzine being, respectively, between 1.1 and 2 to 1 and between 1 and 2 to 1,
  b. heating said mixture to a fluidizing temperature at which said carbonyl-substituted hydroxybenzene and said dialkyl sulfate form a substantially homogeneous liquid medium and said sodium carbonate is suspended in said medium,
  c. maintaining said mixture at a temperature at least equal to said fluidizing temperature, d. stirring said mixture thereby to promote an alkylation reaction in said mixture and produce a carbonyl substituted alkoxybenzene from said hydroxybenzene, and e. adding lubricating water to said mixture during said alkylation reaction in amount just sufficient to maintain said mixture stirrable during said reaction.

2. The method according to claim 1 wherein said dialkyl sulphate is dimethyl sulfate.

3. The method according to claim 1 wherein said mixture is maintained at a temperature between 60° and 100° C.

4. The method according to claim 1 wherein said mixture is maintained with agitation at said temperature until substantially all hydroxyl substituents on said substituted hydroxybenzene are converted to alkoxyl substituents.

5. The method according to claim 1 wherein the substituted alkoxybenzene is separated from said mixture by adding hot water to said mixture and extracting the substituted alkoxybenzene by solvent extraction.

6. The method according to claim 1 wherein the substituted alkoxybenzene is separated from said mixture by adding water to said mixture, cooling said mixture to solidify the alkoxybenzene product and separating the solidified alkoxybenzene product from the aqueous mixture.

7. The method of claim 1 wherein the amount of lubricating water added to the mixture will be not greater than the initial weight of said hydroxybenzene compound in said mixture.

8. A process for the preparation of 3,4,5-trimethoxybenzaldehyde, comprising:

a. forming a mixture consisting essentially of a substituted hydroxybenzaldehyde of the group consisting of syringealdehyde, 5-hydroxyveratradehyde and 5-hydroxyvanillin with dimethyl sulfate and sodium carbonate, the molar ratios of said dimethyl sulfate and of said sodium carbonate to said hydroxybenzene being, respectively, between 1.2 and 2 to 1 and between 1 and 2 to 1;

b. heating said mixture to a fluidizing temperature at which said substituted hydroxybenzaldehyde and dimethyl sulfate form a substantially homogeneous liquid mexium and said carbonate is suspended in said medium, and c. maintaining said mixture at a temperature at least equal to said fluidizing temperature, d. stirring said mixture thereby to promote a methylation reaction in said mixture and produce a substituted methoxybenzaldehyde from said hydroxybenzaldehyde; and e. adding lubricating water to said mixture during said methylation reaction in an amount just sufficient to maintain said mixture stirrable during said reaction.

9. The process of claim 8 wherein said mixture is maintained with agitation at a temperature between 75° and 100° C.

10. The process of claim 8 wherein said 3,4,5-trimethoxybenzaldehyde is separated from said mixture.

* * * * *